United States Patent
Odle et al.

(10) Patent No.: US 6,576,770 B1
(45) Date of Patent: Jun. 10, 2003

(54) PREPARATION OF SUBSTITUTED PHTHALIC ANHYDRIDES AND SUBSTITUTED PHTHALIMIDES

(75) Inventors: Roy Ray Odle, Mt. Vernon, IN (US); Thomas Link Guggenheim, Mt. Vernon, IN (US); Philip L. Angermeier, Mt. Vernon, IN (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/683,259

(22) Filed: Dec. 5, 2001

(51) Int. Cl.[7] ..................... C07D 307/89; C07D 209/48
(52) U.S. Cl. ....................................... 548/485; 549/248
(58) Field of Search ................................ 549/248, 485

(56) References Cited

U.S. PATENT DOCUMENTS

| | | |
|---|---|---|
| 1,891,843 A | 12/1932 | Shaw et al. |
| 2,391,226 A | 12/1945 | Clifford et al. .......... 260/342.4 |
| 2,764,597 A | 9/1956 | Barney .................... 260/346.3 |
| 3,240,792 A | 3/1966 | Patrick et al. ........... 260/346.3 |
| 3,346,597 A | 10/1967 | De Acetis ................ 260/346.3 |
| 3,480,667 A | 11/1969 | Siegart et al. .............. 260/514 |
| 3,506,689 A | 4/1970 | Peterlein .................. 260/346.3 |
| 3,803,085 A | 4/1974 | Takehoshi et al. |
| 3,819,658 A | 6/1974 | Gormley et al. ......... 260/346.3 |
| 3,875,116 A | 4/1975 | Heath et al. |
| 3,879,428 A | 4/1975 | Heath et al. |
| 3,972,902 A | 8/1976 | Heath et al. ............. 260/346.3 |
| 3,983,093 A | 9/1976 | Williams, III et al. |
| 4,045,408 A | 8/1977 | Griffith et al. ................ 260/47 |
| 4,217,281 A | 8/1980 | Markezich et al. ..... 260/326 A |
| 4,257,953 A | 3/1981 | Williams, III et al. .. 260/326 R |
| 4,273,712 A | 6/1981 | Williams, III et al. |
| 4,302,396 A | 11/1981 | Tsujimoto et al. ....... 260/346.3 |
| 4,318,857 A | 3/1982 | Webb et al. ............. 260/346.3 |
| 4,329,291 A | 5/1982 | Webb et al. ................. 549/241 |
| 4,329,292 A | 5/1982 | Webb ........................ 549/241 |
| 4,329,496 A | 5/1982 | Webb ........................ 562/468 |
| 4,340,545 A | 7/1982 | Webb et al. ................. 549/241 |
| 4,374,267 A | 2/1983 | Fifolt et al. ................. 562/549 |
| 4,417,044 A | 11/1983 | Parekh ........................ 528/179 |
| 4,455,410 A | 6/1984 | Giles, Jr. .................... 525/436 |
| 4,514,572 A | 4/1985 | Hamprecht et al. ......... 549/246 |
| 4,517,372 A | 5/1985 | Tang .......................... 549/246 |
| 4,520,204 A | 5/1985 | Evans |
| 4,559,405 A | 12/1985 | Telschow .................... 549/240 |
| 4,560,772 A | 12/1985 | Telschow et al. ........... 549/240 |
| 4,560,773 A | 12/1985 | Telschow .................... 549/240 |
| 4,571,425 A | 2/1986 | Silva .......................... 549/241 |
| 4,584,388 A | 4/1986 | Webb ........................ 549/241 |
| 4,599,429 A | 7/1986 | Odle .......................... 548/481 |
| 4,612,361 A | 9/1986 | Peters |
| 4,675,376 A | 6/1987 | Peters |
| 4,680,412 A | 7/1987 | Hamprecht et al. ......... 548/480 |
| 4,902,809 A | 2/1990 | Groeneweg et al. ........ 548/481 |
| 4,921,970 A | 5/1990 | Odle .......................... 548/480 |
| 4,962,206 A | 10/1990 | Cocoman et al. ........... 549/246 |
| 4,965,337 A | 10/1990 | Peters et al. |
| 4,978,760 A | 12/1990 | Spohn ........................ 549/246 |
| 5,003,088 A | 3/1991 | Spohn et al. ............... 549/246 |
| 5,021,588 A | 6/1991 | Contractor ................. 549/259 |
| 5,049,682 A | 9/1991 | Tang et al. ................. 549/246 |
| 5,059,697 A | 10/1991 | Fertel et al. ................ 549/246 |
| 5,132,423 A | 7/1992 | Brunelle et al. ............ 544/162 |
| 5,155,234 A | 10/1992 | Odle .......................... 549/243 |
| 5,206,391 A | 4/1993 | Seper et al. ................. 549/246 |
| 5,229,482 A | 7/1993 | Brunelle .................... 528/125 |
| 5,233,054 A | 8/1993 | Tang et al. ................. 549/246 |
| 5,235,071 A | 8/1993 | Ueda et al. ................ 549/248 |
| 5,266,678 A | 11/1993 | Perry et al. ................ 528/322 |
| 5,300,201 A | 4/1994 | Seper et al. ............. 204/157.6 |
| 5,322,954 A | 6/1994 | Seper et al. ................ 549/246 |
| 5,359,084 A | 10/1994 | Dellacoletta et al. |
| 5,359,092 A | 10/1994 | Hay et al. ..................... 546/99 |
| 5,364,824 A | 11/1994 | Andrews et al. ............ 502/209 |
| 5,459,227 A | 10/1995 | Hay et al. ................... 528/211 |
| 5,510,308 A | 4/1996 | Kourtakis ................... 502/209 |
| 5,536,846 A | 7/1996 | Dellacoletta et al. |
| 5,557,005 A | 9/1996 | Semler et al. ................ 560/47 |
| 5,672,750 A | 9/1997 | Perry ......................... 564/132 |
| 5,683,553 A | 11/1997 | Baur et al. ..................... 203/1 |
| 5,705,685 A | 1/1998 | Lyons et al. ................ 562/549 |
| 5,719,295 A | 2/1998 | Dellacoletta et al. |
| 5,750,777 A | 5/1998 | Aubry et al. ............... 562/549 |
| 5,779,792 A | 7/1998 | Atami et al. ................ 117/214 |
| 5,792,719 A | 8/1998 | Eberle et al. ............... 502/178 |
| 5,872,294 A | 2/1999 | Caringi et al. .............. 564/240 |
| 5,908,915 A | 6/1999 | Brunelle |
| 5,936,099 A | 8/1999 | Dellacoletta et al. |
| 6,008,374 A | 12/1999 | Dellacoletta et al. |
| 6,011,122 A | 1/2000 | Puyenbroek |
| 6,072,010 A | 6/2000 | Puyenbroek |
| 6,235,866 B1 | 5/2001 | Khouri et al. |
| 6,265,521 B1 | 7/2001 | Fyvie et al. |

FOREIGN PATENT DOCUMENTS

JP          10237063        9/1998

*Primary Examiner*—Taofiq Solola

(57) ABSTRACT

A process for the formation of halophthalic anhydrides and halogen substituted-n-alkyl-phthalimides from the corresponding substituted-n-alkyl-tetrahydrophthalimide by passing said substituted-n-alkyl-tetrahydrophthalimide over a metal catalyst, in the gaseous phase in the presence of oxygen. By selection of the reaction temperature and reaction time, high conversions and purity of the anhydride or imide can be selectively obtained.

14 Claims, No Drawings

PREPARATION OF SUBSTITUTED PHTHALIC ANHYDRIDES AND SUBSTITUTED PHTHALIMIDES

CROSS REFERENCE TO RELATED APPLICATIONS

Not applicable.

FEDERAL RESEARCH STATEMENT

Not applicable.

BACKGROUND OF INVENTION

The disclosure relates to a process for the formation of substituted phthalic anhydrides and substituted-N-alkyl-phthalimides from the corresponding substituted-N-alkyl-tetrahydrophthalimides. This disclosure particularly relates to a process for the formation of halophthalic anhydrides and halogen substituted-N-alkyl-phthalimides from the corresponding halogen substituted-N-alkyl-tetrahydrophthalimides.

The increasing importance of high performance polyimides has led to an interest in substituted phthalic anhydrides, especially halophthalic anhydrides. Halophthalic anhydrides are particularly useful as intermediates for the preparation of dianhydride monomers, such as oxydiphthalic anhydride which may be co-polymerized with a suitable diamine to form a condensation polyimide. The preparation of dianhydride monomers for the high performance polymer industry requires halophthalic anhydrides of very high purity, since the presence of even what normally would be considered as minor amounts of impurities would degrade the polymer product and perhaps render the product unsuitable for certain uses.

It is known that 3-chlorophthalic anhydride can be obtained by oxidation of 3-chloro-o-xylene with, for example, nitric acid at elevated temperature and elevated pressure and subsequent conversion to the anhydride of the 3-chlorophthalic acid formed in the oxidation. The isomerically pure 3-chloro-o-xylene is obtained by distillative separation of the products of the nuclear chlorination of o-xylene, but this distillative separation is extremely complicated because of the low boiling point differences (relative volatilities) of 3- and 4-chloro-o-xylene. An industrial column for the simultaneous preparation of 3-chloro-o-xylene and 4-chloro-o-xylene in purities of, in each case, above 99% needs, in the case of continuous operation, approximately 250 theoretical separation stages. Other separation processes for separating the isomers, such as fractional crystallization, are no less complicated.

Nanophthlaic anhydrides may also be prepared by the aromatization of halo-substituted saturated or partially saturated phthalic anhydrides. Substituted tetrahydrophthalic anhydrides may be aromatized using a halogen such as bromine or chlorine, a brominating agent, phosphorous pentoxide, excess sulfur in combination with a catalytic amount of zinc oxide and 2-mercaptobenxothiazole, palladium, or activated carbon in the absence of air. Each of these approaches to aromatization suffers from drawbacks such as the production of highly corrosive by-products, low yields, decarboxylation, and difficulty in the isolation of the desired product.

3-Chlorophthalic anhydride can also be prepared from 3-nitrophthalic anhydride by replacement of the nitro group by chlorine. The 3-nitrophthalic anhydride needed for this is prepared in three process steps by nitration of phthalic anhydride in moderate yield, isomer separation of the nitrophthalic acids formed by fractional crystallization, and conversion to the anhydride. This multistage and complicated route, which additionally gives poor yields, is not very suitable for industrial use.

The chlorination of phthalic anhydride using Lewis acid catalysts leads to mixtures that contain not only the two isomeric 3- and 4-chlorophthalic anhydrides, which are separable by distillation, but also more highly chlorinated phthalic anhydrides. Specialized distillation equipment is required to separate the desired isomer from the close boiling points mixture.

Although the chemical literature discloses a variety of methods for the preparation of substituted phthalic anhydrides, it will be appreciated that a need continues to for a more economical and efficient process, suitable for the preparation of high purity halophthalic anhydrides.

SUMMARY OF INVENTION

The needs discussed above have been generally satisfied by the discovery of a process for the formation of halophthalic anhydrides comprising heating a halogen substituted-N-alkyl tetrahydrophthalimide in the presence of a metal catalyst and an oxygen containing gas.

In another aspect, a process for the formation of halogen substituted-N-alkyl-phthalimide comprises heating a halogen substituted-N-alkyl tetrahydrophthalimide in the presence of a metal catalyst and an oxygen containing gas.

BRIEF DESCRIPTION OF DRAWINGS

Not applicable.

DETAILED DESCRIPTION

As indicated above, this invention relates to a novel process for the formation of halophthalic anhydrides and halogen substituted-N-alkyl-phthalimides from the corresponding halogen substituted-N-alkyl-tetrahydrophthalimide by passing the halogen substituted-N-alkyl-tetrahydrophthalimide over a metal catalyst, preferably vanadium oxide, in the gaseous phase in the presence of an oxygen containing gas. By selection of the reaction temperature, reaction time, and catalyst, high conversions and purity of the substituted anhydride or imide can be selectively obtained.

In a first embodiment, a halogen substituted-N-alkyl-tetrahydrophthalimide of the formula

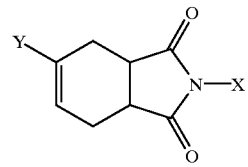

where Y is a halogen and X is a straight chain or branched alkyl moiety having 1 to about 18 carbons is heated in the gaseous phase in the presence of a metal catalyst and an oxygen containing gas to result in a halophthalic anhydride of the formula

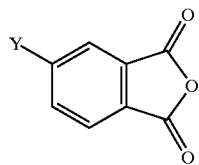

In a second embodiment, a halogen substituted-N-alkyl-tetrahydrophthalimide of the formula

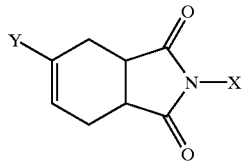

where Y is a halogen and X is straight chain or branched alkyl moiety having 1 to about 18 carbons is heated in the gaseous phase in the presence of a metal catalyst and oxygen to result in a halogen substituted-N-alkyl-phthalimide of the formula

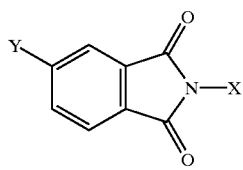

In a third embodiment, a halogen substituted-N-alkyl-tetrahydrophthalimide of the formula

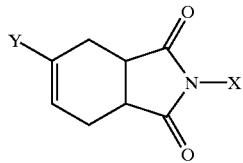

where Y is a halogen and X is a straight chain or branched alkyl moiety having 1 to about 18 carbons is passed, in the gaseous phase, over vanadium oxide in the presence of oxygen at a temperature and rate sufficient to result in at least a 90% conversion of the halogen substituted-N-alkyl-tetrahydrophthalimide to a halophthalic anhydride of the formula

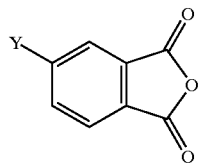

In a fourth embodiment, a halogen substituted-N-alkyl-tetrahydrophthalimide of the formula

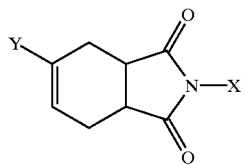

where Y is a halogen and X is a straight chain or branched alkyl moiety of having 1 to about 18 carbons is passed over, in the gaseous phase, a metal catalyst in the presence of oxygen at a temperature and rate sufficient to result in at least a 90% conversion of the halogen substituted-N-alkyl-tetrahydrophthalimide to a halogen substituted-N-alkyl-phthalimide of the formula

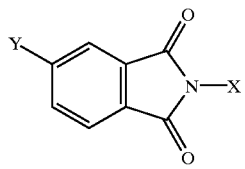

These and other embodiments will become apparent in the detailed description of the invention that follows.

The starting material for the formation of halophthalic anhydrides and halogen substituted N-alkyl-phthalimides is 4-halo-N-alkyl-tetrahydrophthalimide of the formula

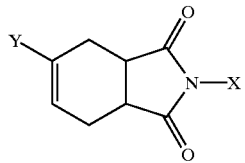

wherein Y is a halogen and X is a straight chain or branched alkyl moiety having 1 to about 18 carbons in length. These compounds are conveniently prepared by the known Diels-Alder reaction of the 2-halo-1,3-butadiene with maleic anhydride to result in the 4-halo-tetrahydrophthalic anhydride of the formula

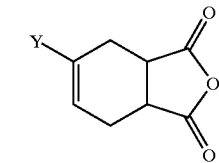

wherein Y is a halogen, preferably chlorine. A detailed description of the methods of synthesizing these starting materials is disclosed in U.S. Pat. No. 5,003,088 to Spohn.

It was discovered that side reactions, such as decarboxylation and carbon formation, could be avoided by converting the anhydride to the imide for the aromatization reaction. The anhydride is imidized with a primary amine, preferably straight chain or branched alkyl amine having 1 to about 18 carbons, using standard techniques of the art to afford the 4-halo-N-alkyl-tetrahydrophthalimide.

In some embodiments, chloroprene, maleic anhydride, and methyl amine are utilized as the precursors to result in a 4-halo-N-alkyl-tetrahydrophthalimide of the formula

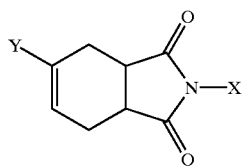

wherein Y is chlorine and X is methyl.

Suitable catalysts for the conversion of 4-halo-N-alkyl-tetrahydrophthalimide include the platinum, palladium, rhodium, ruthenium, rhenium, iridium, copper or nickel, either in elemental form or as a metal oxide compound or complex thereof, either unsupported or on a suitable support. Other suitable catalysts include copper chromite, which is believed to have the formula $CuO\ Cr_2O_3$, chromium oxide, molybdenum oxide, tungsten oxide, and vanadium oxide.

Useful catalyst supports include, for example, activated carbon, charcoal, silicon carbide, silica gel, alumina, acidic silica-alumina, silica, titania, zirconia, kieselguhr, mixed rare earth oxides, carbonates, barium carbonate, barium sulfate, calcium carbonate, pumice, silica alumina mixtures, zeolites, and the like. Supported catalysts, such as those described in U.S. Pat. No 5,792,719 to Erbele containing vanadium oxide are useful.

Preferred catalysts include those comprising a reducible oxide of vanadium supported on a material selected from clays, zeolitic materials of the metallo-silicate or metallo-alumino-phosphate type, and oxides of a second metal selected from Ti, Zr, Zn, Th, Mg, Ca, Ba, Si and Al. These catalysts have superior dehydrogenation activity when the vanadium has a valency such that it is not in its most reduced state. Other suitable catalytic complexes include cuprous oxide, cupric oxide and the $M^0$ compounds where $M^0$ is Pd, Pt, Ni, Rh, or Ru, and is bound in the structure by phosphine, phosphite or carbamyl ligands.

As previously mentioned, preferred catalysts include those containing the oxides of vanadium, for example $V_2O_5$, $V_7O_{13}$, VO, $VO_2$, $V_2O_3$, $V_3O_7$, or mixtures thereof. Especially preferred are catalysts containing $V_2O_5$.

Useful oxygen containing gases include gases or combinations of gases which are a source of molecular oxygen ($O_2$), for example 100% oxygen and mixtures of oxygen with an inert gas with a sufficient concentration of oxygen to effect aromatization. Sufficient oxygen concentrations typically are greater than or equal to about 6% oxygen, preferably greater than or equal to about 15%, more preferably greater than or equal to about 20%. Clearly mixtures with greater than or equal to about 50% oxygen may also be used. As will be appreciated by one of skill in the art, the concentration of oxygen may affect the rate of the reaction. A preferred oxygen containing gas is air.

The aromatization reaction is preferably conducted in the vapor phase. The reaction may be carried out in any suitable reactor configuration. For example, the reaction may be performed in a fixed-bed, moving bed, ebullating bed reactor, or other as is within the ability of the person skilled in the art to determine. A preferred reactor configuration is the fixed-bed reactor.

Typical fixed-bed reactors are, for example, metallic reaction tubes that are collected into tube-bundle reactors and are surrounded by a heat exchange medium. Generally, the reaction tubes are arranged vertically and the reaction mixture flows through them from the top. The reaction tubes are generally surrounded by a heat exchange medium that serves the dual purpose of both heating the tubes and removing heat from the tube, if necessary.

A portion of the tube contains the catalyst that is fixed in place by means of holders fitted in the vicinity of the lower ends of the tubes. The reaction tubes can, if desired, be charged in layers with catalyst of different types, shapes, and sizes.

The reaction procedure involves heating, for example, 4-chloro-N-methyl-tetrahydrophthalimide until it melts and vaporizes. The vapors are pumped into the reaction tube. Air, or a gas mixture containing oxygen, is also passed into the heated reaction tube. The two gases are mixed as they pass through the tube entering the region of the tube wherein the catalyst is located. The reaction occurs in the catalyst region and the products are vented from the tube into a cooler container allowing the collection of the aromatized compounds. The mechanism of the reaction described above is believed to involve the removal of hydrogens from the saturated ring which unite with the oxygen in the air flow to create water. The water produced is allowed to escape or is trapped in, for example, an aqueous media.

The entry of air, or a gas containing oxygen, into the reactor may be undertaken in several ways. Methods include, for example, using a pressurized flow into the entry end of the reactor tube, or by applying a vacuum to the outlet of the collection and/or trap units. Either method is satisfactory for the movement of the gases through the reactor.

The process may also be conducted by dissolving the starting material in an inert volatile solvent and passing the solution into the heated reactor and allowing vaporization to occur therein, before passage into the section of the reactor containing the catalyst.

When a solution of the starting material is employed, a solvent such as acetic acid is used, and the solution is fed into the reactor by a pump or by gravity where the elevated temperature of the reactor and the air flow vaporizes the solvent solution for passage into the reaction zone containing the catalyst.

The temperature used is that which selectively favors the formation of halo-N-alkyl-phthalimide or halophthalic anhydride as reaction products. The process is preferably run at a temperature in the reaction zone of between about 200° and about 400° C., preferably between about 240° and 350° C. When the temperature of the reaction zone is less than about 290° C. and preferably when the temperature is controlled to 260° C. ±about 10° C., it was unexpectedly found that essentially complete conversion to the halo-N-alkyl-phthalimide could be obtained. Conversely, when the temperature of the reaction zone is above about 290° C. and preferably when the temperature is controlled to 305° C. ±about 10° C., it was unexpectedly found that essentially complete conversion to the halo-phthalic anhydride could be obtained. By essentially complete it is meant that less than about 5% impurities are produced. The determination of the most desirable temperature for a given reaction is within the ability of the person skilled in the art.

Flow rates through the reaction column also affect the degree of conversion and the product distribution obtained. The contact time for halo-N-alkyl-tetrahydrophthalimide within the reaction zone in the presence of the catalyst should be sufficient to provide for essentially complete conversion of the halo-N-alkyl-tetrahydrophthalimide to the halo-N-alkyl-phthalimide or halophthalic anhydride. Thus, the required contact time can vary depending on parameters such as the geometry and dimensions of the reactor system, the density of the catalyst, and the remaining activity of the catalyst. The term "contact time" can be defined as the length of time the starting material, i.e. halo-N-alkyl-tetrahydrophthalimide, and the catalyst are in intimate contact in the reaction zone. As the reaction proceeds and the activity of the catalyst declines, the residence time may be adjusted and made increasingly longer to adapt to the momentary state of the catalyst in such a manner that quantitative conversion is just reached at all times. A diluent gas for adjustment of the space velocity may be used such as, for example, nitrogen, argon, or helium. Reactor conditions can be adjusted without undue experimentation through continuous monitoring of the product distribution through techniques standard in the art. One standard technique is gas chromatography.

After the aromatization reaction, the substituted phthalic anhydride can be used directly for further reactions or may be purified by standard techniques, including crystallization or distillation. If the reactor conditions are operated in a manner that results in aromatization to the substituted-N-alkyl-phthalimide, the imide may also be utilized directly or likewise be purified. The imide may also be converted to the anhydride through hydrolysis and subsequent ring closure. Halo-substituents may also be exchanged for other moieties. For example, chlorophthalic anhydride may be converted to the fluoro-analogue through reaction with potassium fluoride. The fluorophthalic anhydride may subsequently be converted to various ethers, for example, through techniques known in the art.

All patents cited are incorporated herein by reference.

The following specific examples are provided to further illustrate this invention and the manner in which it may be carried out. It will be understood, however, that specific details given in the examples have been chosen for purpose of illustration and are not to be construed as limitations on the invention.

EXPERIMENTAL

Solution Reactions

A mixture of 5 parts by weight of 4-chloro-N-methyl tetrahydrophthalimide and 1 part by weight of catalyst in 73 parts by weight of trichlorobenzene was brought to reflux under a spurge of air. The reaction was maintained at reflux for about 4 hours, with stirring. The reaction mixture was then cooled to about room temperature. Analysis of the reaction product was made using gas chromatography-mass spectrometry. The results are contained in Table 1.

TABLE 1

| Catalyst | time (hr) | yield (%) |
| --- | --- | --- |
| Calgon activated carbon type s-sorb 12 12 × 30 | 4 | 1.6 |
| $V_2O_5$ | 4 | 0 |
| Pt/C | 4 | 1 |
| Pd/C | 4 | 1 |

As noted by the solution data of Table 1, aromatization to the desired halo-N-alkyl-phthalimide or halophthalic anhydride in solution was extremely poor.

Gas Phase Reactions

Gas phase reactions were carried out in a hot-tube reactor that was packed with about 13 grams of a catalyst containing $V_2O_5$. The inlet of the hot-tube reactor was connected to a flow controller and heated syringe pump. The flow controller managed the flow of purified air which was varied according to Tables 2 and 3. The heated syringe pump contained 4-chloro-N-methyl tetrahydrophthalimide and delivered it to the hot tube reactor at a constant rate of 0.05 milliliters per minute. The outlet of the hot tube reactor was connected to a receiver cooled in an ice-bath where the reaction products were collected. The hot-tube reactor was maintained at the desired temperature. The reaction product was analyzed by gas chromatographic techniques after the system had equilibrated for the desired amount of time. Results after 10–20 minutes of equilibration are contained in Table 2. Results after 30 minutes of equilibration are contained in Table 3.

TABLE 2

| | Flow of Air | | |
| --- | --- | --- | --- |
| Temp. (° C.) | 40 ml/min | 90 ml/min | 140 ml/min |
| 260 | 84% SM | 0% SM | 9% SM |
| | 14% ClPI | 100% ClPI | 91% ClPI |
| | 0% DeCl | 0% DeCl | 0% DeCl |
| | 0% ClPA | 0% ClPA | 0% ClPA |
| 305 | 0% SM | 0% SM | 0% SM |
| | 71% ClPI | 4% ClPI | 0% ClPI |
| | 4% DeCl | 1% DeCl | 3% DeCl |
| | 24% ClPA | 95% ClPA | 97% ClPA |
| 350 | 0% SM | 0% SM | — |
| | 12% ClPI | 0% ClPI | — |
| | 5% DeCl | 10% DeCl | — |
| | 80% ClPA | 87% ClPA | — |

SM = 4-chloro-N-methyl tetrahydrophthalimide, ClPI = 4-chloro-N-methyl phthalimide; DeCl = dechlorination by-product; ClPA = 4-chlorophthalic anhydride

TABLE 3

| | Flow of Air | |
| --- | --- | --- |
| Temp. (° C.) | 40 ml/min | 90 ml/min |
| 260 | 1% SM | 8% SM |
| | 99% ClPI | 92% ClPI |
| | 0% DeCl | 0% DeCl |
| | 0% ClPA | 0% ClPA |
| 280 | 0% SM | 2% SM |
| | 100% ClPI | 93% ClPI |
| | 0% DeCl | 2% DeCl |
| | 0% ClPA | 2% ClPA |

SM = 4-chloro-N-methyl tetrahydrophthalimide, ClPI = 4-chloro-N-methyl phthalimide; DeCl = dechlorination by-product; ClPA = 4-chlorophthalic anhydride As noted by the gas phase reaction data contained in Tables 2 and 3, reaction condition selection can lead to either the 4-chloro-N-methyl phthalimide or 4-chlorophthalic anhydride directly. It was unexpected that conditions could be established, e.g., 305° C., wherein very high conversions directly to the anhydride could be directly achieved from the imidized starting material. Likewise it was unexpected that conditions could be established, e.g., at 260° C., to achieve essentially quantitative aromatization to 4-chloro-N-methyl phthalimide. Given the above information one of ordinary skill in the art could readily manipulate the reaction conditions to optimize the yield of the desired product.

The preceding examples are set forth to illustrate specific embodiments of the invention and are not intended to limit its scope. Additional embodiments and advantages within the scope of the claimed invention will be apparent to one or ordinary skill in the art.

What is claimed is:

1. A process for the preparation of a halogen substituted phthalic anhydride of the formula comprising heating a halogen substituted-N-alkyl-tetrahydrophthalimide of the formula

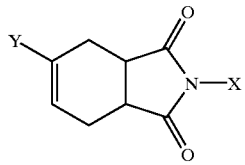

wherein Y is a halogen and X is a straight chain or branched alkyl moiety of from 1 to about 18 carbons to a temperature greater than about 290° C. in the presence of metal catalyst and oxygen-containing gas.

2. The process of claim 1, wherein metal catalyst comprises an oxide of vanadium.

3. The process of claim 1, wherein the oxygen containing gas is air.

4. The process of claim 1, wherein the temperature of the process and the flow of the halogen substituted-N-alkyl-tetrahydrophthalimide over the metal catalyst is at a rate sufficient to result in a conversion of at least 90% to the corresponding substituted phthalic anhydride.

5. The process of claim 1, wherein the temperature of the process is 305° C.±about 10° C.

6. The process of claim 1, wherein Y is chlorine.

7. A process for the preparation of a halogen substituted-N-alkyl-phthalimide of the formula

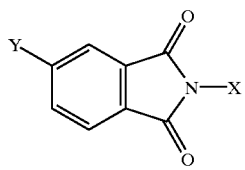

comprising heating a halogen substituted-N-alkyl-tetrahydrophthalimide of the formula

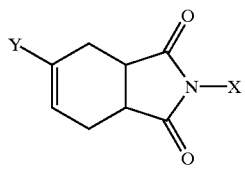

wherein Y is a halogen and X is a straight chain or branched alkyl moiety of from 1 to about 18 carbons in the gaseous phase to a temperature less than about 290° C. in the presence of metal catalyst and oxygen-containing gas.

8. The process of claim 7, wherein the temperature and flow rate of the process is sufficient to result in a conversion of at least 90% of the halogen substituted-N-alkyl-tetrahydrophthalimide to the corresponding halogen substituted N-alkyl-phthalimide.

9. The process of claim 7, wherein metal catalyst comprises an oxide of vanadium.

10. The process of claim 7, wherein the oxygen containing gas is air.

11. The process of claim 7, wherein the temperature of the process is 260° C.±about 10° C.

12. The process of claim 7, wherein Y is chlorine.

13. A process for the preparation of a halogen substituted phthalic anhydride of the formula

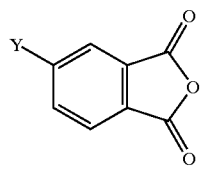

comprising passing a halogen substituted-N-alkyl-tetrahydrophthalimide of the formula

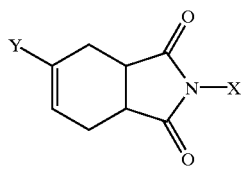

wherein Y is a halogen and X is a straight chain or branched alky moiety of 1 to about 18 carbons over vanadium oxide in the presence of oxygen at a temperature and rate sufficient to result in at least a 90% conversion of the halogen substituted-N-alkyl-tetrahydrophthalimide to the halogen substituted phthalic anhydride.

14. A process for the preparation of a halogen substituted-N- alkyl-phthalimide of the formula

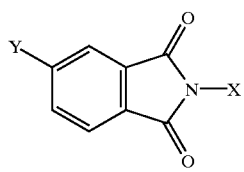

comprising passing a halogen substituted-N-alkyl-tetrahydrophthalimid of the formula

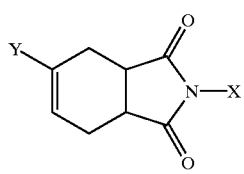

wherein Y is a halogen and X is a straight chain or branched alkyl moiety having 1 to about 18 carbons over vanadium oxide in the presence of oxygen at a temperature and rate sufficient to result in at least a 90% conversion of the halogen substituted-N-alkyl-tetrahydrophthalimide to the halogen substituted-N-alkyl-phthalimide.

* * * * *

UNITED STATES PATENT AND TRADEMARK OFFICE
CERTIFICATE OF CORRECTION

PATENT NO. : 6,576,770 B1  Page 1 of 1
APPLICATION NO. : 09/683259
DATED : June 10, 2003
INVENTOR(S) : Roy Odle et al.

It is certified that error appears in the above-identified patent and that said Letters Patent is hereby corrected as shown below:

Column 1,
Line 24, after "an" insert --increased--,
Line 59, after "and" delete "2-mercaptobenxothiazole" and insert therefor --2-mercaptobenzothiazole--.

Column 2,
Line 17, after "to" insert --exist--.

Column 6,
Line 50, after "the" delete "halo-phthalic" and insert therefor --halophthalic--.

Column 7,
Line 55, after "Table" delete "1,aromatization" and insert therefor --1, aromatization--.

Column 8,
Line 63, after "one" delete "or" and insert therefor --of--.

Column 10,
Line 31, before "moiety" delete "alky" and insert therefor --alkyl--,
Line 48, before "of" delete "tetrahydrophthalimid" and insert therefor --tetrahydrophthalimide--.

Signed and Sealed this

Eleventh Day of July, 2006

JON W. DUDAS
*Director of the United States Patent and Trademark Office*